US006458808B1

(12) United States Patent
Ricci et al.

(10) Patent No.: US 6,458,808 B1
(45) Date of Patent: Oct. 1, 2002

(54) PHARMACEUTICAL COMPOSITION FOR THE TREATMENT OF COGNITIVE CEREBROVASCULAR DISEASE

(75) Inventors: Marcelo A. Ricci; Silvia Krasuk; Joaquina Faour, all of Buenos Aires (AR)

(73) Assignee: Osmotica Corp., Tortola (VG)

( * ) Notice: Subject to any disclaimer, the term of this patent is extended or adjusted under 35 U.S.C. 154(b) by 0 days.

(21) Appl. No.: 09/828,777

(22) Filed: Apr. 9, 2001

(30) Foreign Application Priority Data

Dec. 20, 2000 (AR) ........................ 00 01 07022

(51) Int. Cl.[7] ........................ A61K 31/445; A61K 31/44
(52) U.S. Cl. ........................ 514/321; 514/356; 514/678; 514/922
(58) Field of Search ................................ 514/321, 356, 514/678, 922

(56) References Cited

U.S. PATENT DOCUMENTS

| 4,406,906 A | * | 9/1983 | Meyer et al. ................ 424/263 |
| 5,668,117 A | | 9/1997 | Shapiro |
| 5,827,832 A | | 10/1998 | Sandage, Jr. et al. |
| 6,093,743 A | | 7/2000 | Lai et al. |

OTHER PUBLICATIONS

Dona, G. et al., A Double–Blind Study of the Efficacy of Idebenone . . . , Acta Gerontol. 1988, 38(4): 188–196.

Langley, M.S. et al., Nimodipine: A Review of . . . , Drugs, 1989, 37:669–699.

Dona, G. et al., Double–blind Study to Compare . . . , Acta Gerontol., 1990, 40 (1–2):54–62.

Lingetti, M., Evaluation of the Clinical Efficacy . . . , Acta Gerontol. Geriatr., 1992, 15: 225–237.

Marigliano, V. et al., Randomized, double-blind, . . . , Arch. Gerontol. Geriatr., 1992, 15:239–248.

Senin, U. et al., Idebenone in Senile . . . , Arch. Gerontol. Geriatr., 1992, 15:249–260.

Nappi, G. et al., Long–term Idebenone Treatment . . . , Arch. Gerontol. Geriatr. 1992, 15:261–269.

Bergamasco, B. et al., Idebenone in the Treatment of . . . , 1992, 15:271–278.

Bergamasco, B. et al. Effects of Idebenone in Elderly . . . , Arch. Gerontol. Geriatr., 1992, 15:279–286.

Gillis, J. C. et al., Idebenone . . . , Drugs & Aging, 1994, 5 (2):133–152.

Weyer, G. et al., Efficacy and Safety of Idebenone . . . , Human Psychopharmacology, vol. 11:53–65. (1994).

Canade, V. et al. Effetti della Nimodipina . . . , Minerva Medica, 82:111–114 (1995).

\* cited by examiner

*Primary Examiner*—Frederick Krass
(74) *Attorney, Agent, or Firm*—Rick Matos; Innovar, L.L.C.

(57) ABSTRACT

A pharmaceutical composition comprising idebenone in synergistic combination with nimodipine for the treatment of cognitive disorders of cerebrovascular origin.

19 Claims, No Drawings

PHARMACEUTICAL COMPOSITION FOR THE TREATMENT OF COGNITIVE CEREBROVASCULAR DISEASE

FIELD OF THE INVENTION

This invention relates to a pharmaceutical composition for the treatment of cognitive disorders of cerebrovascular origin, which comprises idebenone in synergistic combination with nimodipine.

BACKGROUND OF THE INVENTION

Cerebrovascular disease has three etiopathogenesies that cause brain injury. The etiology of cardiac embolism has a well-defined treatment using anticoagulant agents. The typical treatment for obstructive etiology of main arteries, carotid and vertebral, is surgery and use of platelet antiaggregant agents. The third etiology is the disease of small brain penetrating arteries. The pathogenesis of sick arterioles is a fibrohyaline, lipohyaline, amyloid or eosinophil deposit and thickening. In cases of abnormally small brain arterioles there exists controversy as regards treatment, and for secondary prophylaxis of new episodes, platelet antiaggregants are also used.

Mild to moderate cognitive cerebrovascular disease is generally manifested through an impairment in attention and memory, behavioral and relation disorders, abulia, lack of interest and poor personal care.

A branch of clinical-neurological research is based on the concept of neuroprotection, providing the brain tissue with an optimized metabolism that may tolerate an intermediate state of injury, so that if a reduction in blood flow to the brain, ranging from 30 to 20 ml/100 g of tissue/minute, causes an ischaemic injury to the cells, it will remain potentially reversible.

Idebenone is a benzoquinone which pharmacodynamic properties have been established in the line of drugs with cytoprotecting effects, as described in U.S. Pat. No. 4,271,083. Idebenone is the general name of 6-(10-hydroxydecil)-2,3-dimethoxy-5-methyl-1,4-benzoquinone compound. Data from in vitro essays (mitochondrial preparations of rat and dog brain) suggest that the cytoprotecting action of idebenone is achieved by facilitating the conveyance of electrons in the mitochondrial respiratory cycle, inhibiting lipid peroxidation, reducing non-breathing oxygen consumption and stimulating ATP formation.

Effects on memory and learning capabilities have been tested on animals, attenuating the abnormal amnesic and learning behavior as induced by brain ischemia.

Idebenone is widely delivered to different tissues, including the brain, and is detected in eleven different regions of the brain.

Oral administration of idebenone to healthy. volunteers, either in an single dose or in multiple doses of 45 or 100 mg, reaches a maximum concentration in plasma in an average period of 1 to 2 hours. Accumulation does not occur after repeated doses.

Therapeutic potential of this substance is in cognitive deterioration, especially in those patients having vascular problems that tend to worsen.

Nimodipine is a non-symmetrical dihydropyridine in respect of ester groups of positions 3- and 5-, as disclosed in U.S. Pat. No. 3,799,934, wherein it is described as a coronary vasodilator agent having anti-hypertension properties, as well. Nimodipine is the general name for the 1,4-dyhidro-5-(isopropoxycarbonyl)-2,6-dimethyl-4-(3-nitrophenyl)-3-pyridine-carboxylate of 2-methoxyethyl compound. In U.S. Pat. No. 4,406,906 the use of nimodipine for the treatment of brain insufficiencies is disclosed, in particular those related to insufficiencies in brain vascular circulation. Further studies and researches disclose that nimodipine, as a lipophilic ester, crosses the blood-brain barrier. The preferred action site of the drug is over the brain flow and calcium cell homeostasis. One hypothesis about pharmacological action relates to regulation of cell membrane mechanisms that preserve appropriate calcium concentration. The failure of these systems results in an elevation of intracell calcium, which is considered as cytotoxic, causing an activation of calcium-dependent proteases and perturbations of cell cytoskeleton. Such situations related to calcium displacement have been assessed in basic tests on smooth muscle cell isolated from the vessels.

Several studies have been performed on human beings in order to measure the effects of nimodipine action on patients with brain ischemia. Results of some of them show an improvement in the cognitive functioning in sick people with vascular dementia.

SUMMARY OF THE INVENTION

Surprisingly, the present inventors have found that the joint administration of nimodipine and idebenone provides a therapeutic effect that is superior to that provided by each compound alone.

Therefore, this invention provides a new pharmaceutical composition for the prophylaxis and treatment of cognitive cerebrovascular disease which includes synergistically effective amounts of idebenone in combination with nimodipine.

It is a further object of the invention to provide a method for the prophylaxis or treatment of cognitive cerebrovascular disease in a mammal, which comprises the administration to a mammal of an effective amount of idebenone in combination with nimodipine.

It is still another object of the invention to use idebenone in combination with nimodipine for the preparation of a pharmaceutical composition for the prophylaxis or treatment of cognitive cerebrovascular disease.

Other features, advantages and embodiments of the invention will be apparent for those skilled in the art from the description below, the accompanying examples and appended claims.

DETAILED DESCRIPTION OF THE INVENTION

The pharmaceutical composition of the present invention can be orally administered in the form of doses prepared from the admixture of each of the active compounds of idebenone and nimodipine with a pharmaceutically acceptable carrier or excipient.

It should be understood that the use of pharmaceutically acceptable nimodipine salts are also within the scope of the present invention.

The pharmaceutical composition of the present invention can be furnished in alternative dosage forms according to the processes as follows: (i) active compounds are optionally admixed with pharmaceutically acceptable excipients, by any pharmaceutical technique already known, so as to provide a dosage form; (ii) active compounds are processed separately with pharmaceutically acceptable excipients, for further combination in a dosage form; or (iii) compounds are processed separately with pharmaceutically acceptable excipients, for providing independent dosage forms which shall be administered as a set.

Preferably, the pharmaceutical composition of the invention is provided as an oral administration form which comprises the combination of idebenone and nimodipine. Oral administration forms can be tablets, lozenges, capsules, granules, and the like.

The pharmaceutical composition of this invention can be prepared by those known processes using excipients such as binders, disintegrants, lubricants, tablet glidants, tablet opaquants, colorants and other additives which use is known in the art.

Exemplary excipients are sucrose, lactose, glucose, starch, mannitol, sorbitol, cellulose, talc, and cyclodextrins.

As used in the present invention, "tablet binders" mean any substance that cause adhesion of powder particles in the granulation of a tablet. Such compounds are exemplified by, but not limited to, gum arabic, alginic acid, tragacanth, sodium carboxy-methylcellulose, (poly)vinylpirrolidone); compressible sugar (e.g., NuTab), ethylcellulose, gelatin, liquid glucose, methylcellulose, povidone, pregelatinized starch, polyethylene glycol, sucrose, starch, collagen, albumin, polyethylene oxide, mycrocristalline cellulose and combinations thereof, as well as other materials that are well known to those of ordinary skill in the art.

As used in the present invention, the term "tablet disintegrants" means those compounds used in solid dosage forms, to promote disintegration of the solid mass in smaller particles which are more easily dispersed or dissolved. Such compounds include by way of example and without limitation, starch, such as corn starch, potato starch, pregelatinized and modified starches, sweeteners, clays such as bentonite, microcrystaline cellulose (e.g., Avicel), calcium carboxymethylcellulose, potassium polyacriline cellulose (e.g., Amberlite), alginates, sodium starch glycolate, gums such as agar, guar gum, locust bean, pectin, tragacanth, and combinations thereof, as well as other materials that are well known to those of ordinary skill in the art.

As used in the present invention, the term "tablet lubricants" means substances used in the formulation for reducing friction during tablet compression. Such compounds include by way of example and without limitation, calcium stearate, magnesium stearate, mineral oil, stearic acid, zinc stearate, and combinations thereof, as well as other materials that are well known to those of ordinary skill in the art.

As used in the present invention, the term "tablet glidants" means those agents used in tablet and capsule formulation for improving granulation fluidity. Such compounds include by way of example and without limitation, colloidal silica, calcium silicate, magnesium silicate, silica hydrogel, corn starch, talc and combinations thereof, as well as other materials that are well known to those of ordinary skill in the art.

As used in the present invention, the term "tablet or capsule opaquant" means those compounds used for achieving an opaque coating over the tablets or capsules to provide an opacity that can help in photostabilization in the case of photosensitive agents. Such compounds include by way of example and without limitation, titanium dioxide, and other materials that are well known to those of ordinary skill in the art.

Whenever necessary, the composition can be provided in a sustained release dosage form.

Preferred dosage forms are those having 10 to 1000 mg of idebenone and 6 to 600 mg of nimodipine.

Certainly, administered dosage should be carefully determined according to age, weight and condition of the person being treated, and also according to administration form, and dosage form and regime. Satisfactory results can be obtained through oral administration of 0.15 to 15 mg of ibedenone/kilogram of body weight/day in combination with 0.1 to 10 mg of nimodipine/kilogram of body weight/day. An adequate dosage for prophylaxis or treatment of mild to moderate cerebrovascular disease should comprise about 90 mg/day of idebenone in combination with 60 mg/day of nimodipine. Preferably, two daily doses, orally administered, of a dosage form having 45 mg of idebenone and 30 mg of nimodipine will provide satisfactory results.

The composition of the invention can be used in the treatment of symptoms associated to mild to moderate cerebrovascular disorders, such as memory and attention alterations, behavioral and relation disorders, deficit in personal care, and the like.

As explained below, the synergistic action of the combination of ibedenone and nimodipine produces therapeutic effects superior to those provided by each drug separately, combining synergistically their respective effects, such as: activation of metabolism, increasing ATP production, replacement of neuronal energetic reserve, capture of free radicals, reestablishing of neurotransmitting process, selective blockade of calcium channels in arteries and neuron protection of neurovascular structure, prophylaxis of neurological deficit due to cerebrovascular insufficiency.

The following formulation and examples are included in order to better illustrate the invention, but these examples shall not be considered a limitation to the invention, the scope of which is established in the appended claims.

EXAMPLE 1

Preferred Formulation for a Tablet

| Ingredient | Amount |
| --- | --- |
| Nimodipine | 30.0 mg |
| Idebenone | 45.0 mg |
| Povidone (PVP K30) | 95.0 mg |
| Microcrystalline cellulose | 380.0 mg |
| Sodium Croscarmellose | 45.0 mg |
| Colloidal silica dioxide | 6.0 mg |
| Magnesium stearate | 4.0 mg |
| Hydroxypropylmethyl cellulose | 7.4 mg |
| Polyethylene glycol 6000 | 1.4 mg |
| Copolyvidone | 5.72 mg |
| Talc | 6.0 mg |
| Lacquer Yellow D&C No. 10 | 0.5713 mg |
| Lacquer Yellow Sunset No. 6 | 0.7137 mg |
| Titanium dioxide | 5.36 mg |

EXAMPLE 2

Clinical Trial

Material

Seventy nine patients having either mild or very mild cognitive deterioration with the following inclusion criterion:

Both, male and female patients, from 50 to 85 years old.

Antecedents of ischaemic cerebrovascular pathology with symptoms or only with expression in brain computerized tomography (silent infarct). In case of focal or acute multimodal symptoms, at least a three-month period should elapse since symptoms evidence before being included in the tests.

According to computerized tomography of the brain all patients showed a deep injury of the lacunar type (smaller than 15 mm in diameter), which could be a single injury. or multiple injuries, or isolated leukoaraiosis or in combination with lacuna.

Severity of cognitive deterioration was of the very mild or mild type CDR scale 0,5 and 1 (Clinical Dementia Rating).

Each patient evidenced a clinic condition so as to be an active part in the neuropsychological tests, and also they were able to ingest medicines, either by themselves or with the help of relatives or persons who took care of them.

Each patient gave a written consent.

In order to avoid new cerebrovasular injuries, patients used only drugs of platelet anti-aggregant activity: aspirin and tyclopidine.

No anti-depressive drugs were used.

Exclusion criteria were as follows:

Myocardial acute infarction for the last six months and/or unbalanced cardiac insufficiency.

Antecedents of acute cerebrovascular symptoms in the last three months.

Cognitive deterioration with CDR equal or higher than 2.

Severe hepatic or renal failure.

Prior psychotic diseases or organic mental syndrome not related to the cerebrovascular disease.

Antecedents of hematological, neoplastic or dysendocrine diseases.

Significant brain ventricle dilation, with an Evans rate higher than 0.32.

Vascular injury larger than 15 mm in diameter according to extensive computerized tomography of the brain.

Method

Patients were selected from the Neurology area of four different hospitals. In each center a randomization list for parallel groups was established. Tablets in the three groups had the same aspect so as to preserve the double-blind characteristic of the study.

For diagnosis of cognitive deterioration and its association to ischaemic cerebrovascular disorders the criteria proposed in 1992 by the California University, USA, were used, in both their probable and possible forms.

Probable Vascular Dementia a) evidence of 2 or more cerebrovascular injuries per history, neurological exams or cerebral computerized tomography, one injury at brain level;

b) if it were a single episode, with a definite time relation with the onset of dementia;

c) early walking disorders of the subcortical type and urinary incontinence with no justification on a peripheral cause, and d) slow progression of symptoms.

Either a) or b) should exist, to which c) or d) can be added.

Possible Vascular Dementia a) antecedents or evidence of a single cerebrovascular episode without a defined time relation with the onset of dementia.

b) no cerebrovascular episode and dementia is associated to an early manifestation of walking disorders of subcortical type and urinary incontinence along with changes expanded over the white substance, both previous and subsequent, in the brain computerized tomography (leukoaraiosis=L-A).

The degree of severity of the cognitive disorder is limited to a borderline, mild condition, according to CDR scale in its points 0.5 and 1. A Hamilton test is carried out in order to detect a depressive condition, which shall contribute to the differential diagnosis of a pseudo dementia.

After these clinical trials were completed, a non contrasting cerebral computerized tomography was taken, which selected patients bearing small subcortical brain vascular injuries, smaller than 15 mm and leukoaraiosis. In computerized tomography of the brain, patients showed vascular origin injuries related to the disease of small brain arteries.

Patients were considered to be hypertensive if in two records they reach a level equal or higher than 160/90 or if they were administered hypotensive medicines due to a previous diagnosis of arterial hypertension.

A clinical history was prepared and exams were performed so as to detect risk factor of vascular disease.

Also data on the degree of education of the patient were taken. In those cases where a patient was suspected or evidenced of a carotid disease with severe stenosis, the patient was excluded. Also patients having probable sources of cardiac embolism were excluded.

This allowed the formation of a subtype of ischaemic cerebrovascular disease corresponding to group III of TOAST, which corresponds to the disease of small arteries.

The Barthel index was used for evaluation of everyday life.

During the initial period a washing in medicine intake was made, in the weeks −4 to 0, the latter being the baseline for those drugs considered to be vasoactive or nootropic.

Platelet anti-aggregant medicines were accepted so as to avoid acute recurrences of the ischaemic vascular disease, in patients who were receiving these medicines or if the researcher considered its incorporation to be appropriate.

The observation period lasted 16 weeks, so patients were randomized in three groups which received as double-blind treatment:

Idebenone 45 mg, twice a day.

Nimodipine 30 mg, twice a day.

Idebenone 45 mg+Nimodipine 30 mg, twice a day.

Therapeutic efficacy criteria were based on the results of Folstein's, CDR and Barthel's scales and Global Clinical Impression (GCI). In order to evaluate therapeutic efficacy between the group receiving the combined dosage and the groups receiving the idebenone or nimodipine alone, a statistically significant improvement in one of the following criteria should exist:

Criterion 1 a) Improvement of at least 1 in CDR or Barthel.

b) Improvement in GCI and/or Folstein.

Criterion 2 a) Improvement of at least 1 in CDR or Barthel.

b) No change in GCI and/or Folstein.

Criterion 3 a) No change in CDR or Barthel.

b) Improvement in GCI and Folstein.

Results—Conclusions

After the observation period was completed, a casuistic of 79 patients was gathered and after the randomization key was opened a biostatistical study of all variables was conducted, which results are shown in the Table below:

| Treatment groups | A | B | C | |
|---|---|---|---|---|
| Number of individuals | 25 | 26 | 28 | |
| Age (average) | 71.8 | 74.6 | 70.0 | 0.04 |
| Basal variables | | | | "p" |
| Sex (masculine) | 64.0% | 38.5% | 35.7% | 0.08 |
| Systolic pressure | 144 | 147.3 | 150.2 | NS |
| Diastolic pressure | 87.2 | 88.6 | 86.9 | NS |
| Anthropometric data | There were no meaningful differences in weight and height | | | |
| Tomographies | There were no significant differences in the type of lesions | | | |
| CDR, Barthel's, Folstein's tests | No significant basal differences | | | |

According to the observed results, we conclude that the three groups were statistically equivalent when initially included into the study.

After the 16-week treatment period was completed, the results obtained were as follows:

| Group | A | B | C |
|---|---|---|---|
| CDR test | 0.68–0.64 | 0.67–0.63 | 0.65–0.63 |
| BARTHEL's test | 87.2–87.6 | 80.7–81.1 | 87.1–87.9 |
| FOLSTEIN's test | 22.8–24.8 (0.0001) | 22.5–23.9 (0.0007) | 22.3–25.6 (0.000001) |
| Global Clinic Impression | 5.0 | 4.9 | 5.73 |

Global Clinical Impression: Code 1: highly worsened—2: worsened—3: minimal worsening—4: unchanged—5: slightly improved—6: improved—7: highly improved.

After the treatment was concluded, CDR showed a slight deterioration with a mark of 0.63 to 0.68 and Barthel's showed an acceptable level in the capacity for everyday life with a mark of 80.7 to 87.9, average. No statistically significant changes were observed either in the CDR or in the Barthel's rate in any of the three groups of patients, when comparing initial starting versus final mark.

Folstein's test showed favorable changes (a higher mark) when comparing initial values to final values in the three groups treated.

According to the results above, the therapeutic efficacy criterion number 3 is accomplished, as above stated, specifically unchanged CDR and Barthel's tests along with favorable modification in Folstein's test and in Global Clinical Impression.

Comparison Between the Three Groups

Comparison of the three groups shows a favorable statistically significant change in group C, in the Folstein's test:

C (nimodipine+idebenone) versus A (idebenone) with p=0.04

C (nimodipine+idebenone) versus B (nimodipine) with p=0.003.

Favorable changes are observed in attention and to a lesser degree in evocation and orientation.

A statistically significant favorable change is also observed when comparing the groups between each other related to the Global Clinical Impression at the end of the study, wherein the superiority of nimodipine+idebenone combination (group C) is observed in comparison to idebenone alone (p=0.0004) and in comparison to nimodipine alone (p=0.0001).

In conclusion, in this patient group with very mild or mild cognitive disorders of cerebrovascular origin, an improvement in cognitive tests is observed with the combination of nimodipine-idebenone which exceeds in a statistically significant way the improvement observed with nimodipine or idebenone used alone.

The descriptions above are detailed descriptions of the particular embodiments of the invention. It should be understood that other descriptions different to those herein can be made within the scope of the present invention and those skilled in the art shall develop modifications thereto. Those skilled in the art, while acknowledging the present invention, should understand that different changes to the aspects herein described can be made, with similar or equal results without departing from the spirit and scope of the invention. The embodiments disclosed herein can be made and implemented without undue experimentation, in light of the present disclosure.

We claim:

1. A pharmaceutical composition for the prophylaxis or treatment of cognitive cerebrovascular disease, comprising a synergistically effective combination of idebenone and nimopidine.

2. A pharmaceutical composition according to claim 1, comprising 10 mg to 1,000 mg of idebenone and 6 to 600 mg of nimopidine.

3. A method of preparing a pharmaceutical composition according to claim 1 or 2, comprising the step of combining idebenone and nimopidine, and optionally one or more excipients.

4. A method for the prophylaxis or treatment of cognitive cerebrovascular disease in a mammal having or at increased risk of having said cerebrovascular disease, comprising the step of administering to said mammal an effective amount of idebenone and an effective amount of nimopidine.

5. The method of claim 4, wherein the idebenone is administered at a daily dosage of 0.15 to 15 mg per kilogram of body weight and the nimopidine is administered at a daily dosage of 0.1 to 10 mg per kilogram of body weight.

6. The method of claim 4 or 5, wherein the idebenone and nimopidine are administered orally.

7. The method of claim 4 or 5, wherein the idebenone is administered at a daily dosage of 45–90 mg and nimopidine is administered at a daily dosage of 30–60 mg.

8. The method of claim 4 or 5, wherein the idebenone and nimopidine provide a synergistic therapeutic effect.

9. The method of claim 4 or 5, wherein symptoms of the cerebrovascular disease are selected from the group consisting of impairment in attention and memory, behavioral and relation disorders, abulia, lack of interest, and poor personal care.

10. The method of claim 4 or 5, wherein the idebenone and nimopidine are administered in the same dosage form.

11. The method of claim 4 or 5, wherein the idebenone and nimopidine are administered in separate dosage forms.

12. The method of claim 4 or 5, wherein the idebenone and nimopidine are administered concurrently.

13. A pharmaceutical dosage form comprising a pharmaceutical composition according to claim 1 or 2.

14. A method for the prophylaxis or treatment of cognitive cerebrovascular disease in a mammal having or at increased risk of having said cerebrovascular disease, comprising the step of orally administering to said mammal 10 to 1000 mg of idebenone and 6 to 600 mg of nimopidine.

15. A method for the prophylaxis or treatment of cognitive cerebrovascular disease in a mammal having or at increased risk of having said cerebrovascular disease comprising the step of orally daily administering to said mammal 0.15 to 15 mg of idebenone per kilogram of body weight and 0.1 to 10 mg of nimopidine per kilogram of body weight, wherein the idebenone and nimopidine provide a synergistic therapeutic effect.

16. The method of claim 15, wherein symptoms of the cerebrovascular disease are selected from the group consisting of impairment in attention and memory, behavioral and relation disorders, abulia, lack of interest, and poor personal care.

17. The method of claim 15, wherein the idebenone and nimopidine are administered in the same dosage form.

18. The method of claim 15, wherein the idebenone and nimopidine are administered in separate dosage forms.

19. The method of claim 15, wherein the idebenone and nimopidine are administered concurrently.

* * * * *